Aug. 10, 1971 D. P. SCHMIDT ET AL Plant Pat. 3,060
MAPLE TREE
Filed Feb. 28, 1969
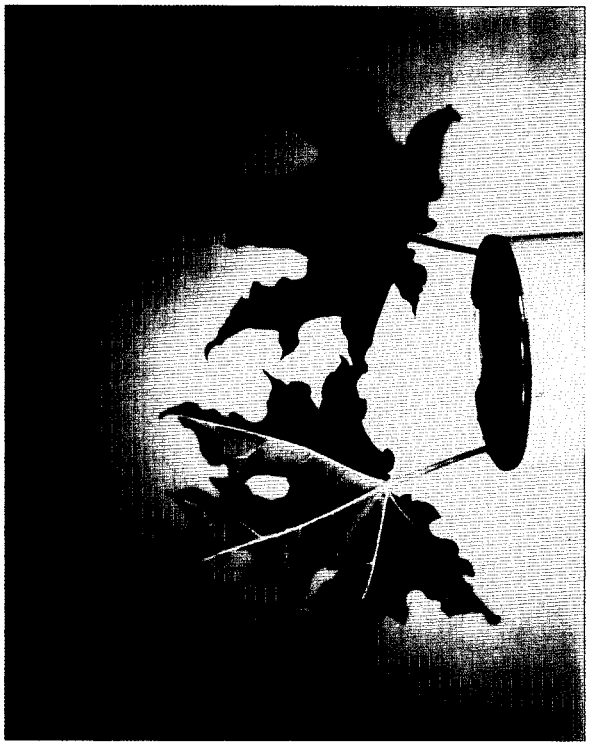
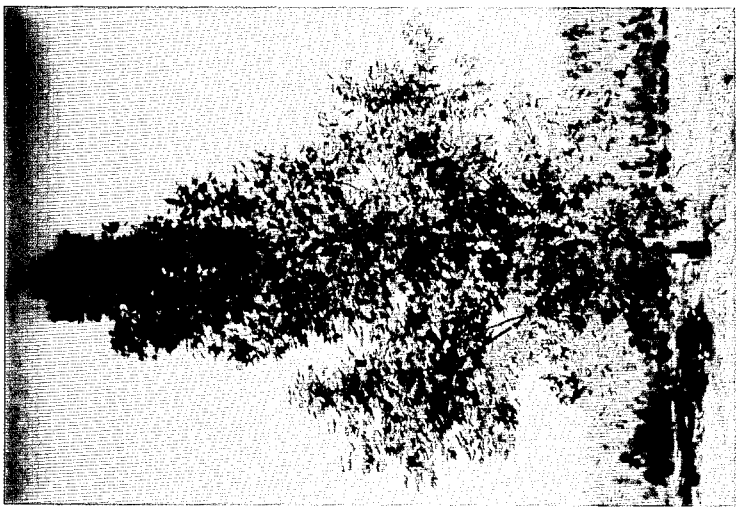
Inventor.
Daniel P. Schmidt, Deceased
By: Jane E. Schmidt, Executrix
By: Robb & Robb
Attorneys.

United States Patent Office

Plant Pat. 3,060
Patented Aug. 10, 1971

3,060
MAPLE TREE

Daniel P. Schmidt, deceased, late of Portland, Oreg., by Jane E. Schmidt, executrix, 18324 NE. Sandy Blvd., Portland, Oreg. 97230

Filed Feb. 28, 1969, Ser. No. 804,721
Int. Cl. A01h 5/12
U.S. Cl. Plt.—51 1 Claim The present invention relates to a new and distinct variety of maple tree which was discovered by the late Daniel P. Schmidt, as a whole tree sport of unknown parentage, in his nursery formerly owned and operated by him in Portland, Multnomah County, Ore.
nursery a group of seedlings of Norway maples (Acer
nursey a group of seedlings of Norway maples (*Acer platanoides*) of unknown parentage. At the end of the first year, his attention was attracted to one particualr tree which bore leaves quite different from those of the other trees in the group which had grown true to form of the species bontanically known as *Acer platanoides*. On closer examination, it was found that this particular tree was apparently a whole tree sport of one of the seedlings of the group in which it was discovered by him. He thereupon took steps to preserve the new sport, keep it under observation, and in due course, to asexually reproduce the same by budding in his nursery aforementioned.

When the sport was first noticed, the leaves thereof were more deeply serrulated and more deeply notched than the leaves of all other adjacent trees or those of all other varieties of maples known to him, and in particular distinctly different from those of the typical *Acer platanoides* species. In addition, the foliage of the new sport was considerably more bushy and heavy and more regular in pattern. Continued observations established that the sport was a strong grower, and by the end of the second year after its original discovery, branches from every bud on the trunk had developed, with the petioles carrying the leaf blades being bright red or reddish bronze in color and standing out in contrast with the green foliage color much more markedly than those of other trees of the species. Still other distinctive features were recognized during continued observations of the original sport and the progeny thereof which were carefully observed and tested over a prolonged period of years.

While the actual parentage of the new sport is not known, it definitely is distinguished from all other maple varieties, as evidenced by the following unique combination of characteristics which are outstanding therein and which represent a valuable improvement from a commercial standpoint:

(1) A vigorous, well-shaped, bushy, free-branching, compact and rapid habit of growth;
(2) A good, natural main stem, with ascending branches, giving the tree a broadly pyramidal shape and an unusually dense form when adequately spaced from other trees;
(3) Abundant foliage when free to develop;
(4) Distinctive, shapely, crinkly, glossy, deeply incised and finely lobed leaves of attractive medium to dark green color overlaid with reddish bronze; and
(5) Distinctive, bright red petioles which attractively and conspicuously contrast with the green leaf color.

The accompanying drawing shows a specimen tree of the new maple variety as photographed shortly after clearing away adjacent trees and other vegetative growth which had inhibited normal development of the branches and foliage, particularly in the lower portion of the tree, and which otherwise would have attained a denser growth and more abundant foliage throughout the tree, at least comparable to the upper portion as shown, if the specimen tree had been adequately spaced from other trees and vegetation; and the drawing also shows the upper and lower surfaces respectively of typical specimen leaves on a larger scale than in the whole tree view, said leaf specimens more nearly depicting the true color of the foliage and being somewhat darker in color than in the view of the whole tree which was photographed in bright sunlight and which made the leaves appear lighter than their normal color which is hereinafter more accurately described.

The following is a detailed description of the new variety, with color terminology in accordance with Wilson's Horticultural Colour Chart, published in collaboration with the Royal Horticultural Society, except where general color terms of ordinary dictionary significance are obvious, and as based on observations of specimens grown at Portland, Ore.

Parentage: Sport of unknown parentage of the species *Acer platanoides*.
Propagation: Holds its distinguishing characteristics through succeeding propagations by budding.
Tree: Medium size; upright; normally dense; bushy; rapid-growing; hardy.
*Trunk*.—Smooth when 10 to 12 years old.
*Branches*.—Freely at intervals of from 4 inches to 6 inches instead of 8 inches to 10 inches which is normal for the species; dense; slender; smooth; ascending. Color—From greenish to slightly carmine at tip when young, but light gray when mature. Lenticels—Small; about 50 per lineal inch on a ¼ inch diameter small main shoot. Color—Light brown.
Foliage:
*Leaves*.—More or less glossy surface and attractively undulate, with sinuses between lobes being noticeably rounded and elevated. Quantity—More abundant than average of the species *Acer platanoides*. Length—Average from 3 inches to 5 inches. Width—Average from 3 inches to 5 inches. Shape—Broadly palmate; variable; markedly sinuate; from 5 to 7 lobed, with main side lobes sometimes exceeding central lobe in length, but the central lobe being longer on the more vigorous shoots; lobes freely and acutely toothed and aristate or drawn to a fine point. Color (mature)—Upper side—Near Ivy Green, Plate 0001060/2. Lower side—Near Spinach Green, Plate 0960/2. Margin—Serrate; sinuate; deeply and variably toothed, with teeth acuminate. Petiole—Medium long; from 2 inches to 6 inches. Color—From green to pink or bright red according to exposure; brighter color than other varieties of the species. Glands—None. Stipules—None.
Flower buds: Not significant.

What is claimed is:

1. A new and distinct variety of maple tree, substantially as herein shown and described, characterized particularly as to novelty by the unique combination of a vigorous, well-shaped, bushy, free-branching, compact and rapid habit of growth, a good, natural main stem, with ascending branches, giving the tree a broadly pyramidal shape, and an unusually dense form, abundant foliage, distinctive, shapely, crinkly, glossy, deeply incised and finely lobed leaves of attractive medium to dark green color overlaid with reddish bronze, and distinctive, bright red petioles which attractively and conspicuously contrast with the green leaf color.

No references cited.

ROBERT E. BAGWILL, Primary Examiner